United States Patent [19]
Volk

[11] Patent Number: 5,745,212
[45] Date of Patent: Apr. 28, 1998

[54] INDIRECT OPHTHALMOSCOPY DEVICE WITH REINVERTING LENS SYSTEM WITH THE REAL INVERTED IMAGE OR CONJUGATE PUPIL FORMED AT LEAST PARTIALLY WITHIN A LENS OF THE REINVERTING LENS SYSTEM

[75] Inventor: Donald A. Volk, Mentor, Ohio

[73] Assignee: Volk Optical, Inc., Mentor, Ohio

[21] Appl. No.: 730,023

[22] Filed: Oct. 11, 1996

Related U.S. Application Data

[60] Provisional application No. 60/005,244 Oct. 11, 1995.
[51] Int. Cl.$^6$ ............................................. A61B 3/00
[52] U.S. Cl. ................................. 351/219; 351/205
[58] Field of Search ............................ 351/219, 205, 351/200, 246, 160 R

[56] References Cited

U.S. PATENT DOCUMENTS

| | | | |
|---|---|---|---|
| 4,721,378 | 1/1988 | Volk | 351/205 |
| 5,200,773 | 4/1993 | Volk | 351/219 |
| 5,523,810 | 6/1996 | Volk | 351/219 |

Primary Examiner—Hung X. Dang
Attorney, Agent, or Firm—Spencer & Frank

[57] ABSTRACT

An indirect ophthalmoscopy lens device includes a plurality of lenses for collecting light emanating from a patient's eye and focussing the light to form a first, real, inverted image of the fundus of the patient's eye outside of the eye, and for reinverting the first, real, inverted image to form an erect image anterior of the device. The first, real, inverted image, rather than being an aerial image, may be formed at least partially within one of the plurality of lenses of the device. A conjugate pupil image, rather than being located in air as an aerial image of the patient's pupil, may be formed within one of the plurality of lenses of the device.

17 Claims, 7 Drawing Sheets

INDIRECT OPHTHALMOSCOPY DEVICE WITH REINVERTING LENS SYSTEM WITH THE REAL INVERTED IMAGE OR CONJUGATE PUPIL FORMED AT LEAST PARTIALLY WITHIN A LENS OF THE REINVERTING LENS SYSTEM

CROSS-REFERENCE TO RELATED APPLICATIONS

The present application claims the right of priority with respect to Provisional application Ser. No. 60/005,244 filed on Oct. 11, 1995, the subject matter of which is incorporated herein by reference.

BACKGROUND OF THE INVENTION

The present invention relates to an indirect ophthalmoscopy lens device that includes an image reinverting system. More particularly, the invention relates to an improved contact or non-contract indirect ophthalmoscopy lens device for use with a slit lamp or other biomicroscope that incorporates a plurality of lens elements that cooperate to provide an upright and erect aerial image of the eye fundus.

My prior U.S. Pat. No. 5,200,773 discloses an indirect ophthalmoscopy contact lens device which includes such a reinverting system. In that device a contact lens element collects light rays which originate at the fundus of a patient's eye, pass through the pupil and exit the cornea. A condensing lens system anterior of the contact lens element refracts the light rays to form a first inverted aerial image of the fundus. This aerial inverted image of the fundus is then erected or reinverted by a prismatic or optical relay system to form a real, erect image of the fundus which can then be observed through a biomicroscope.

The length of such a indirect ophthalmoscopy lens device ideally should be as short as possible in order to reduce the overall distance from the patient's eye to the viewing system such as a slit lamp biomicroscope or to minimize the overall height of the device when resting on the patient's eye, for example during vitreoretinal surgery. According to the above-mentioned U.S. Pat. No. 5,200,773, the first real image is formed as an aerial image anterior to an image forming lens system. However, the creation of the first real image in air may impose a limitation on the extent to which the overall length of the device, including the reinverting system, can be minimized. U.S. Pat. No. 4,721,378 discloses a non-contact indirect ophthalmoscopy lens device which includes a similar image erecting or reinverting lens system. The distances between each of the elements of the device disclosed in this patent are specific to the corresponding front and back focal lengths of the lenses comprising the system. Additionally, both the first real, inverted image and conjugate pupil, defined as the region where the chief rays intersect and cross the optical axis of the system, are formed in air in a similar specific relationship to the front and back focal lengths of the lenses comprising the system. As such, a device made according to this patent will have substantial length.

SUMMARY OF THE INVENTION

It is an object of the present invention to provide an indirect ophthalmoscopy lens device with a reinverting lens system which has an overall length that is shorter than the length of similar prior art devices and yet still produces a high quality image.

It is another object of the present invention to provide an indirect ophthalmoscopy device with an reinverting lens system wherein the first real image is produced partially or completely within an optical element of the system.

It is another object of the present invention to provide an indirect ophthalmoscopy device with a reinverting lens system wherein the conjugate pupil location within the device is produced partially or completely within an optical element of the system.

I have discovered that it is possible to achieve these objects by designing a novel indirect ophthalmoscopy lens device for both contact and non-contact applications for use with the slit lamp biomicroscope for diagnostic or laser treatment applications or, alternatively, for use with the operating microscope for diagnostic and surgical applications, wherein the first real, inverted image formed by the light rays exiting the patient's eye and passing through the lens system of the device or the conjugate pupil region where light rays intersect and cross the optical axis of the system are either partially or wholly located in one of the lenses of the device. That is, by positioning the real, inverted image and/or the conjugate image of the patient's pupil either partially or wholly in a lens of the indirect ophthalmoscopy device, it is possible to bring the lenses of the system closer together and to concomitantly reduce the overall length of the indirect ophthalmoscopy lens device including the reinverting lens system while still obtaining a well corrected image, free of distortion, astigmatism, and field curvature, including an apparent image curvature associated with systems of substantially high power. Such a lens system departs significantly from that of the prior art, both actually and conceptually.

DETAILED DESCRIPTION OF THE PREFERRED EMBODIMENTS

FIGS. 1 to 6 show various lens layouts with an overlaid ray tracing. Although the ray tracings show light proceeding as parallel bundles from an entrance pupil in air, the ray tracings through the lens system follow the same pathways as do light rays which originate at the retina and proceed through the vitreous humor, crystalline lens aqueous humor and cornea of the eye to the various lens elements of the invention embodiments. The use of parallel bundles in air is a simplified representation of the optical system of the emmetropic human eye and is shown represented in all optical system layouts herein. The pupil location in air in the figures is represented by the line referred to herein as pupillary plane P, with the chief light rays passing through a focus centered within the pupil location. The corresponding position of the cornea "C" on an optical axis "A" in relation to the lens elements depicted is shown in FIGS. 1 through 6.

Figure 1:
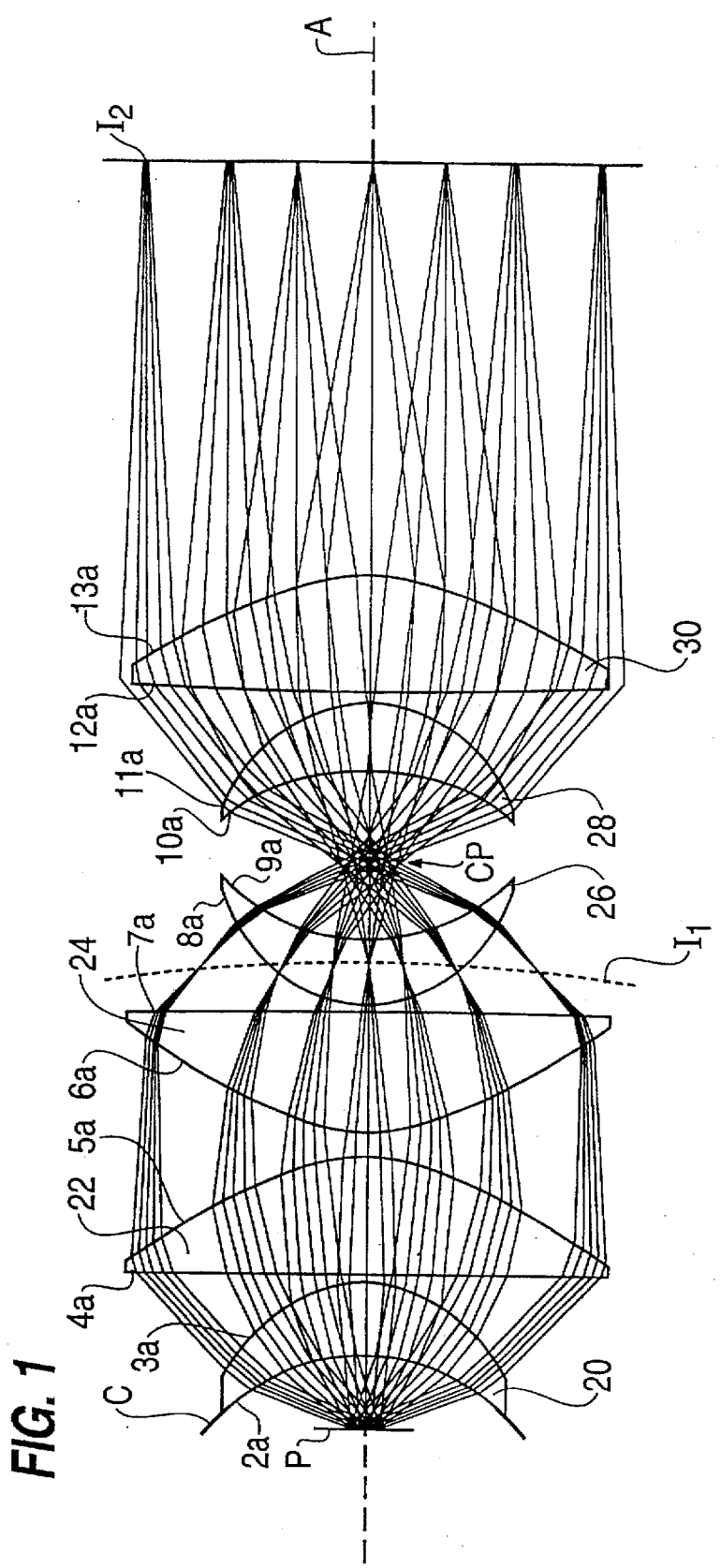
FIG. 1 is a lens layout and ray tracing diagram according to a first embodiment of the invention.

Referring to FIG. 1, there is shown a lens layout for an indirect ophthalmoscopy contact lens device containing a reinverting lens system according to the invention. The indirect ophthalmoscopy contact lens device includes a contact lens 20 having a concavo-convex shape followed by first and second anterior lenses 22 and 24, both having, in this example, a plano convex shape and being oriented with their convex surfaces facing each other. Following plano convex lens 24 in the anterior direction is a pair of meniscus-shaped lenses 26 and 28 arranged with their concave surfaces facing each other. A final biconvex lens 30 is located anterior of meniscus lens 28. The six lenses 20, 22, 24, 26, 28 and 30 have respective surfaces $2a$ through $13a$, with surface $2a$ being the posterior surface of contact lens element 20 and surface $13a$ being the anterior surface of final anterior lens 30. Although lenses 22 and 24 have been shown in this embodiment as plano-convex lenses, their shape may depart from this design while still maintaining the optical and physical advantages described. Alternatively, concave-convex, or biconvex designs may be used advantageously for either or both lenses.

Table I below provides an example of data defining the shape of the respective lenses and the respective lens surfaces as well as the location of the lenses relative to the cornea of a patient's eye (not shown) according to this embodiment of the invention. The values in the "Radius" column are apical radius values and are either positive or negative values depending on whether the surface is convex or concave, respectively. This convention is used throughout the specification.

TABLE 1

| Surface | Radius (mm) | Conic Constant | Distance From Corneal Apex (mm) | Diameter (mm) |
| --- | --- | --- | --- | --- |
| 2a  | −8.0     | 0     | 0.000000  | 11.5 |
| 3a  | 6.1      | −0.1  | 2.900000  | 11.5 |
| 4a  | Infinity | 0     | 3.225000  | 18.2 |
| 5a  | 9.75     | −1.1  | 7.775000  | 18.2 |
| 6a  | 9.75     | −1.15 | 8.750000  | 18.2 |
| 7a  | Infinity | 0     | 13.300000 | 18.2 |
| 8a  | 5.85     | −0.1  | 13.625000 | 11.7 |
| 9a  | −8.45    | 0     | 16.225000 | 11.7 |
| 10a | −9.1     | 0     | 22.725000 | 11.7 |
| 11a | 5.85     | −0.1  | 25.325000 | 11.7 |
| 12a | 110.0    | −16.0 | 25.650000 | 18.2 |
| 13a | 11.0     | −1.6  | 30.150000 | 18.2 |

All of the surfaces in this example are either spherical, having a conic constant of 0, or aspherical conoids having a negative conic constant value, although it is within the scope of this invention to use non-conoid aspheric curvatures as well as positive conic constant values to advantageously provide image correction and minimize length as indicated by optical optimization. In an exemplary implementation, all of the lenses are made of LAH 58 glass with an index of refraction of 1.883. The lenses are all coaxially arranged on the optical axis A of the device. The distances in Table I are the distances of the respective surfaces from the corneal apex C along the optical axis A. Thus, posterior surface $2a$ is a concave spherical surface having a radius of 8.0, a conic constant of 0, and is placed in contact with the patient's cornea C along optical axis A. The diameter of lens 20 is 11.5 mm, in this case designed for use in conjunction with typical suture down vitrectomy rings which are well known in the art. The thickness of each lens and the spacing of the lenses from one another can be obtained from Table I by differencing the distance of adjacent surfaces from the corneal apex. For example, the thickness of contact lens element 20 is 2.9 mm and the distance between anterior surface $3a$ of contact lens 20 and posterior surface $4a$ of the adjacent anterior lens 22 is 0.325 mm. In this example, a real, erect image is formed in a plane $I_2$ spaced 16 mm from surface $13a$ as described below. The lenses shown in FIG. 1 are fixed in a known manner in a frame or holder (not shown).

In operation, an indirect ophthalmoscopy lens device containing the lens configuration illustrated in FIG. 1 is placed on the cornea of a patient's eye. Light emanating from the patient's fundus passes through the patient's pupil, exits the cornea and passes through contact lens 20. The bundles of light rays are bent toward the optical axis by contact lens 20 and are then focussed and bent further by plano convex lenses 22 and 24 so that the light rays focus in a slightly curved image plane $I_1$ which is located at least partially in meniscus lens 26. The image formed in image at plane $I_1$ is a real image, inverted both vertically and horizontally as is typical with indirect ophthalmoscopy lenses. Anterior surface $9a$ of meniscus lens 26 further refracts and bends the light ray bundles passing through image plane $I_1$ toward a conjugate pupil area CP where the light rays cross the optical axis and are subsequently refracted and bent toward the optical axis by meniscus lens 28 and biconvex lens 30, ultimately resulting in a focusing of the light ray bundles in image plane $I_2$, at which there is formed a real, erect image of the patient's fundus.

As can be seen in FIG. 1, the intermediary image plane $I_1$ is formed at least partially in meniscus lens 26. By forming the intermediary image at plane $I_1$ at least partially in one of the lenses in the system, as opposed to in air between the lenses, the indirect ophthalmoscopy contact lens device with the reinverting lens system according to the invention achieves a significantly shorter length compared to known devices of this type. As can be seen from Table I above, the most anterior surface $13a$ of the device in this example is 30.15 mm from the corneal apex, representing an overall length which allows it to be advantageously used for both diagnostic and especially surgical applications.

Figure 2:
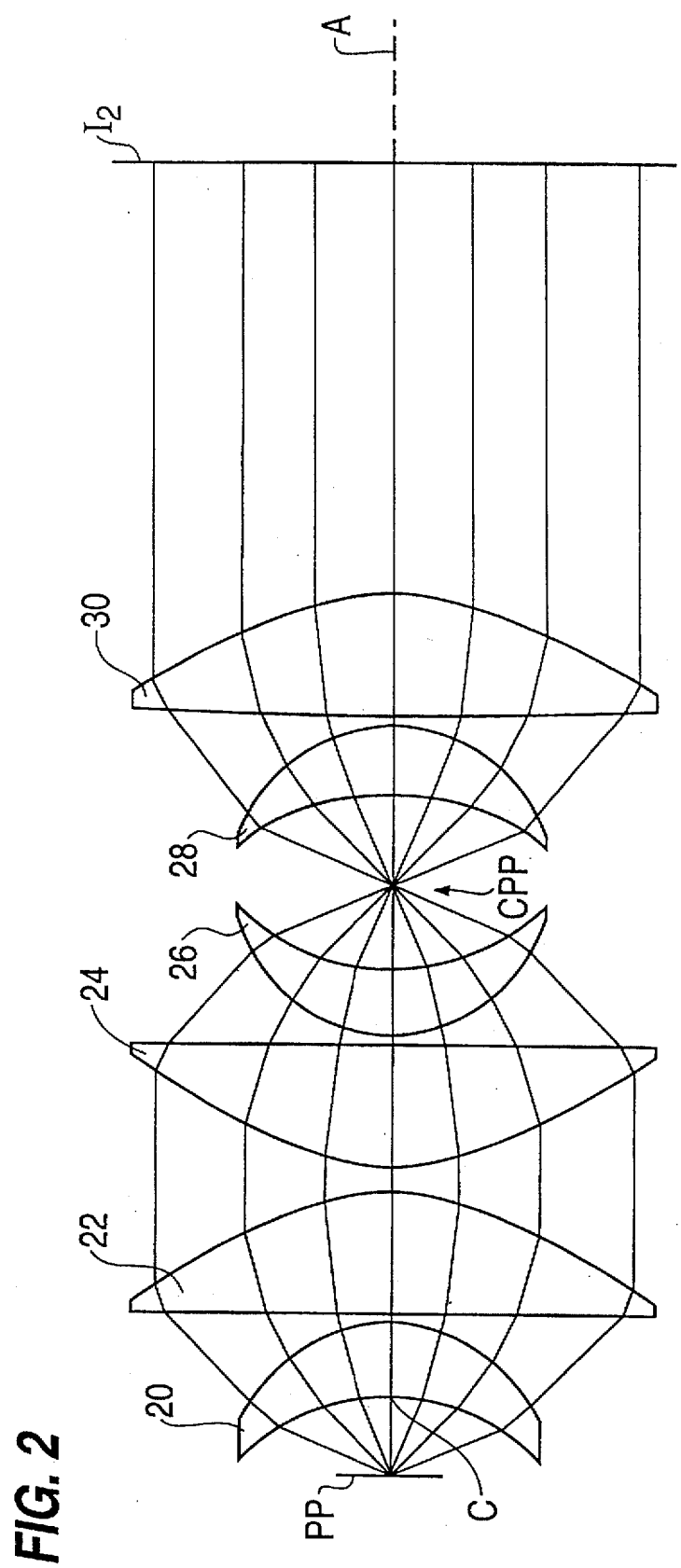
FIG. 2 is a lens layout according to FIG. 1 showing only the path of the principal rays.

FIG. 2 is a lens layout of the same system shown in FIG. 1 combined with a ray tracing which includes only the principal rays, i.e., the central ray of each ray bundle, emanating from the fundus. The principal rays proceed from pupil location PP corresponding to the patient's eye pupil and by virtue of the lens system as described above are caused to meet again at a conjugate pupil location CPP between meniscus lenses 26 and 28 where they cross the optical axis and are brought to focus in image plane $I_2$ to form the real, erect image as previously described.

Figure 3:
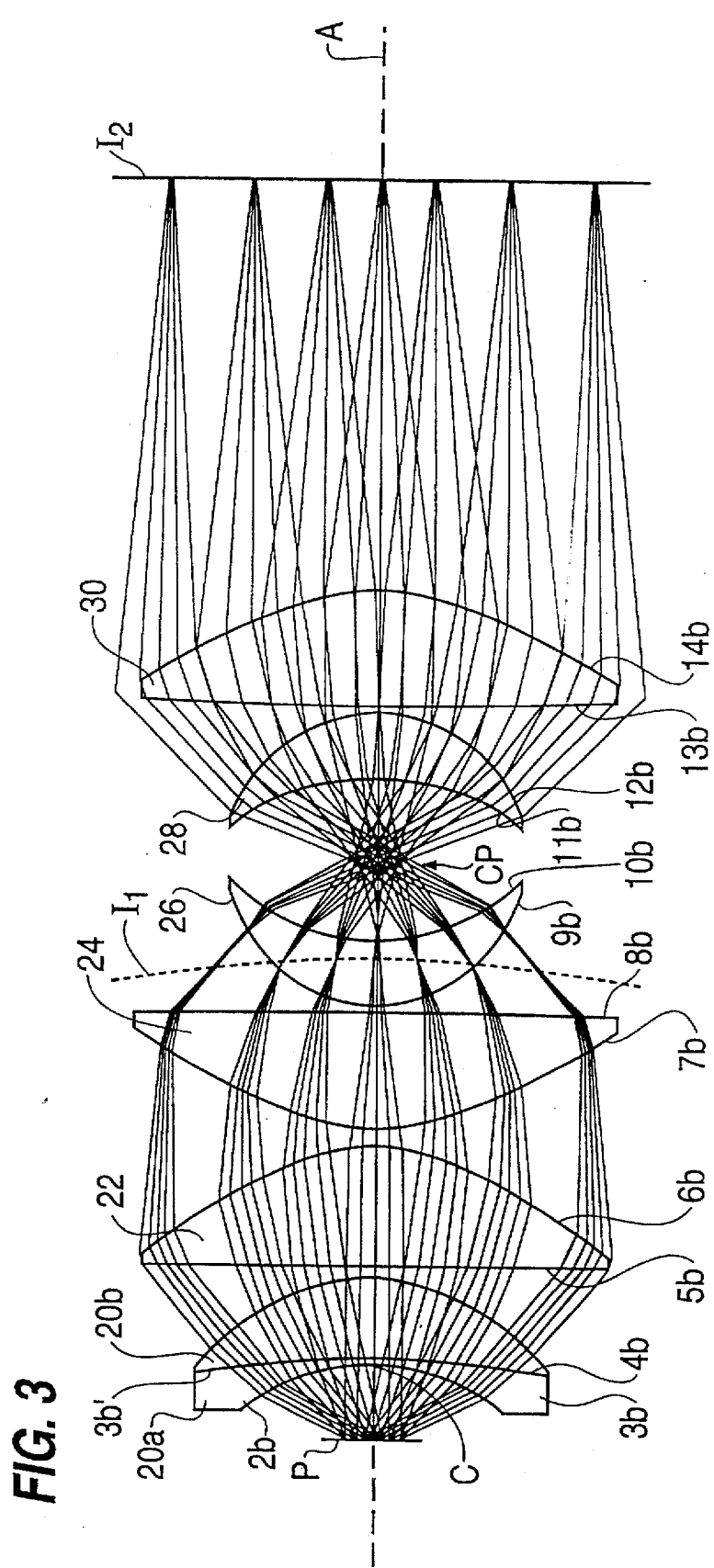
FIG. 3 illustrates a lens layout and ray tracing according to a second embodiment of the invention.

FIG. 3 shows a lens layout and ray tracing of an indirect ophthalmoscopy contact lens device according to a further embodiment of the invention which is similar to the embodiment illustrated in FIGS. 1 and 2 with the exception that the contact lens element comprises a compound contact lens element including, in this example, a posterior acrylic portion $20a$ fixed to an anterior glass portion $20b$ by an optical glue (not shown). The use of a compound contact lens element allows for a greater field of view as more of the peripheral rays are captured due in part to the additional bending that takes place at the interface between posterior acrylic portion $20a$ and the anterior glass portion $20b$ as a result of differing refractive properties of these two portions.

A compound contact lens element of this type is more fully described in my prior U.S. Pat. No. 5,523,810 filed Jun. 5, 1995, the subject matter of which is incorporated herein by reference.

Table II below provides summary data of an exemplary implementation of this embodiment of the invention. In this example, the lenses are all made of LAH 58 glass with the exception of the posterior portion 20a of the compound contact lens which is made of PMMA acrylic. Although not shown or described in relation to the various figures, any of the lens elements of this invention may be made of any glass or plastic material with typical refractive indices ranging from 1.40 to 2.1.

The optical glue fixing contact lens portion 20a to contact lens portion 20b is of a conventional type and has an index of refraction corresponding to one of the contact lens portions as disclosed in my prior patent application mentioned above. The reference numerals 2b through 14b identify the respective lens surfaces of the device illustrated in FIG. 3. Reference numeral 3b' of Table II identifies the anterior surface of contact lens portion 20a and reference numeral 3b identifies the posterior surface of contact lens portion 20b, which surfaces are complimentary to and in intimate contact with one another and thus are defined by the same surface characteristic values. The lens device in this example is still relatively short compared to prior art devices, however, it is slightly longer than the example presented by Table I in connection with FIGS. 1 and 2. In this example, a real, erect image is formed in plane $I_2$ at a distance of 47 mm from the corneal apex, or 16 mm from surface 14b.

TABLE II

| Surface | Radius (mm) | Conic Constant | Distance From Corneal Apex (mm) | Diameter (mm) |
| --- | --- | --- | --- | --- |
| 2b | −8.0 | 0 | 0.000000 | 10.6 |
| 3b | 40.0 | 0 | 0.250000 | 14.0 |
| 3b | −40.0 | 0 | 0.250000 | 14.0 |
| 4b | 7.7 | −0.3984846 | 3.750000 | 14.0 |
| 5b | Infinity | 0 | 4.075000 | 18.2 |
| 6b | 10.5 | −1.1 | 8.625000 | 18.2 |
| 7b | 10.5 | −1.15 | 9.600000 | 18.2 |
| 8b | Infinity | 0 | 14.150000 | 18.2 |
| 9b | 5.85 | −0.1 | 14.475000 | 11.7 |
| 10b | −8.45 | 0 | 16.075000 | 11.7 |
| 11b | −9.1 | 0 | 23.575000 | 11.7 |
| 12b | 5.85 | −0.1 | 26.175000 | 11.7 |
| 13b | 110.0 | −16.0 | 29.500000 | 18.2 |
| 14b | 11.0 | −1.6 | 31.000000 | 18.2 |

The ray tracing of FIG. 3 is similar to the ray tracing of FIG. 1 and illustrates the formation of the intermediary image plane $I_1$ at least partially in the meniscus lens 26. The conjugate pupil area CP is again formed between meniscus lenses and 28 and the final, erect, image is formed in image plane $I_2$ in a similar manner as discussed above in connection with the embodiment of FIGS. 1 and 2.

Figure 4:
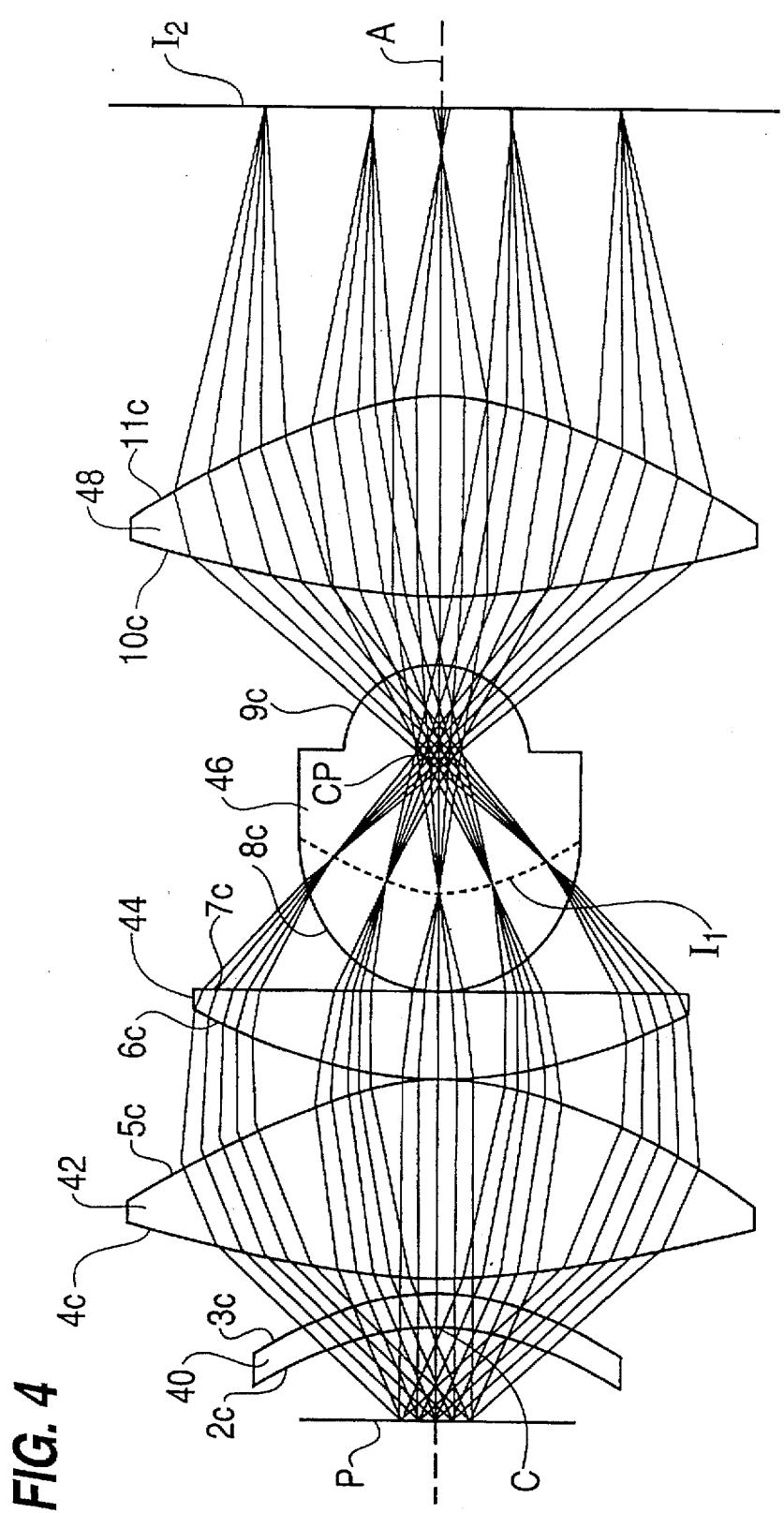
FIG. 4 illustrates a lens layout and ray tracing according to a third embodiment of the invention.

FIG. 4 illustrates yet another embodiment of the invention wherein the image plane $I_1$ is formed entirely within one of the lenses together with the conjugate pupil area. The lens layout in FIG. 4 includes a contact lens element 40 followed in an anterior direction by a biconvex lens 42 which is in turn followed by a plano convex lens 44. A further anterior lens 46 having relatively steep convex surfaces on each side is disposed between plano convex lens 44 and a most anterior biconvex lens 48. Summary data regarding an exemplary implementation of the embodiment of FIG. 4 is presented in Table III. According to an exemplary implementation of the embodiment of FIG. 4, contact lens 40 and anterior lens 46 are both made of PMMA acrylic plastic and the remaining lenses 42, 44 and 48 are made of LAH 58 glass.

TABLE III

| Surface | Radius (mm) | Conic Constant | Distance From Corneal Apex (mm) | Diameter (mm) |
| --- | --- | --- | --- | --- |
| 2c | −7.7 | −0.18 | 0.000000 | 10.0 |
| 3c | 7.7 | 0 | 1.000000 | 10.0 |
| 4c | 14.7167 | −14.0 | 1.500000 | 16.0 |
| 5c | 7.3583 | −2.2 | 7.000000 | 16.0 |
| 6c | 11.0 | 0 | 7.000000 | 13.0 |
| 7c | Infinity | 0 | 9.500000 | 13.0 |
| 8c | 3.5 | −0.3 | 9.500000 | 8.0 |
| 9c | 2.5 | −0.3 | 18.500000 | 5.6 |
| 10c | 14.7167 | −11.0 | 20.000000 | 16.0 |
| 11c | 7.3583 | −1.7 | 26.000000 | 16.0 |

As can be seen, the inverted and reversed first fundus image located in intermediate area image plane $I_1$ is formed wholly within lens 46 along with the conjugate pupil area CP. The reinverted, erect image is formed in image plane $I_2$ which in this example is located 34 mm from the corneal apex.

Figure 5:
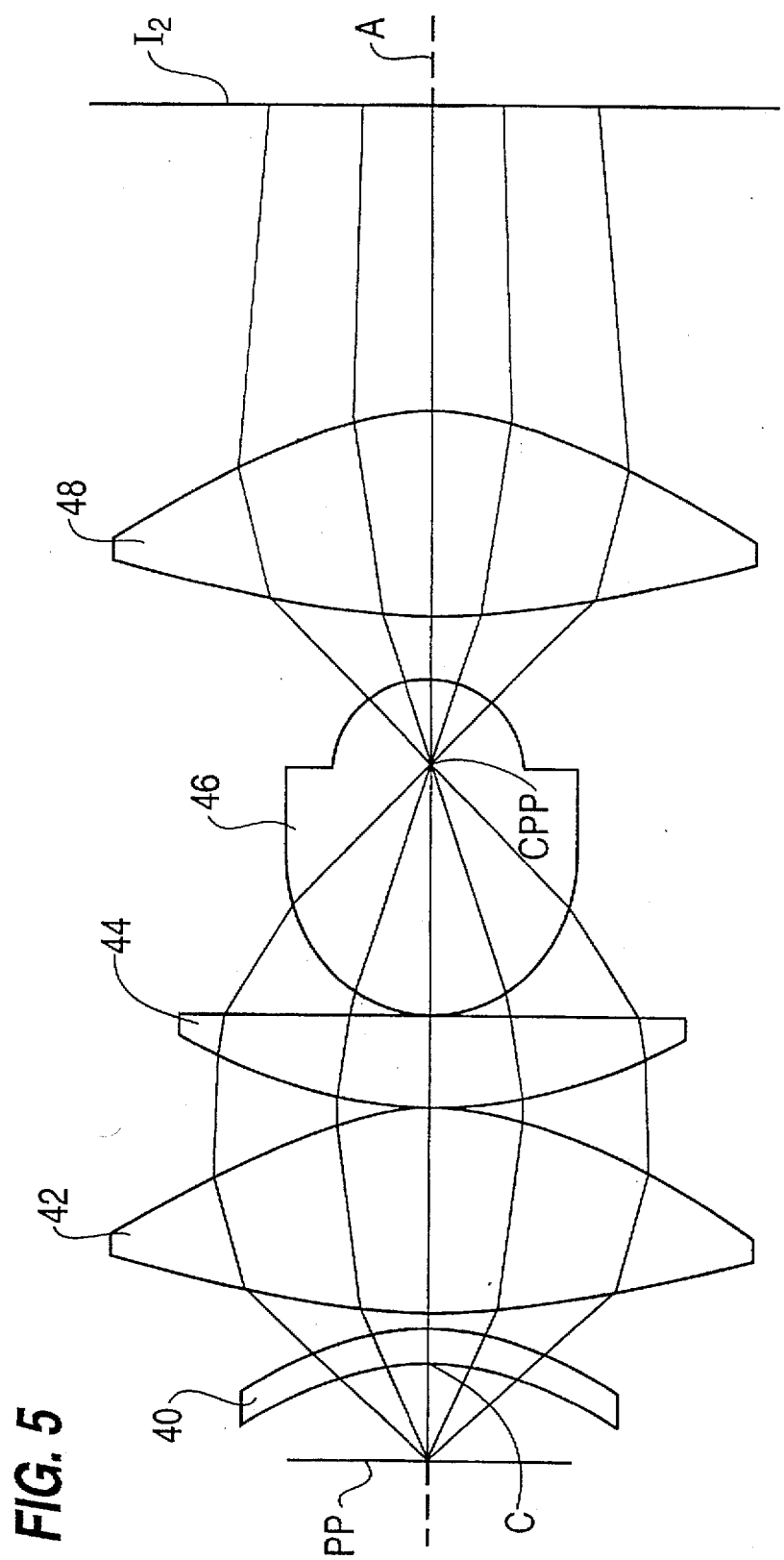
FIG. 5 shows a lens layout according to the embodiment of FIG. 4, with only the path of the principal light rays being illustrated.

FIG. 5 illustrates the same lens layout as FIG. 4 and shows only the principal rays of the ray tracing proceeding from the pupil location PP within the patient's eye and crossing the optical axis at the conjugate pupil location CPP within lens 46.

Figure 6:
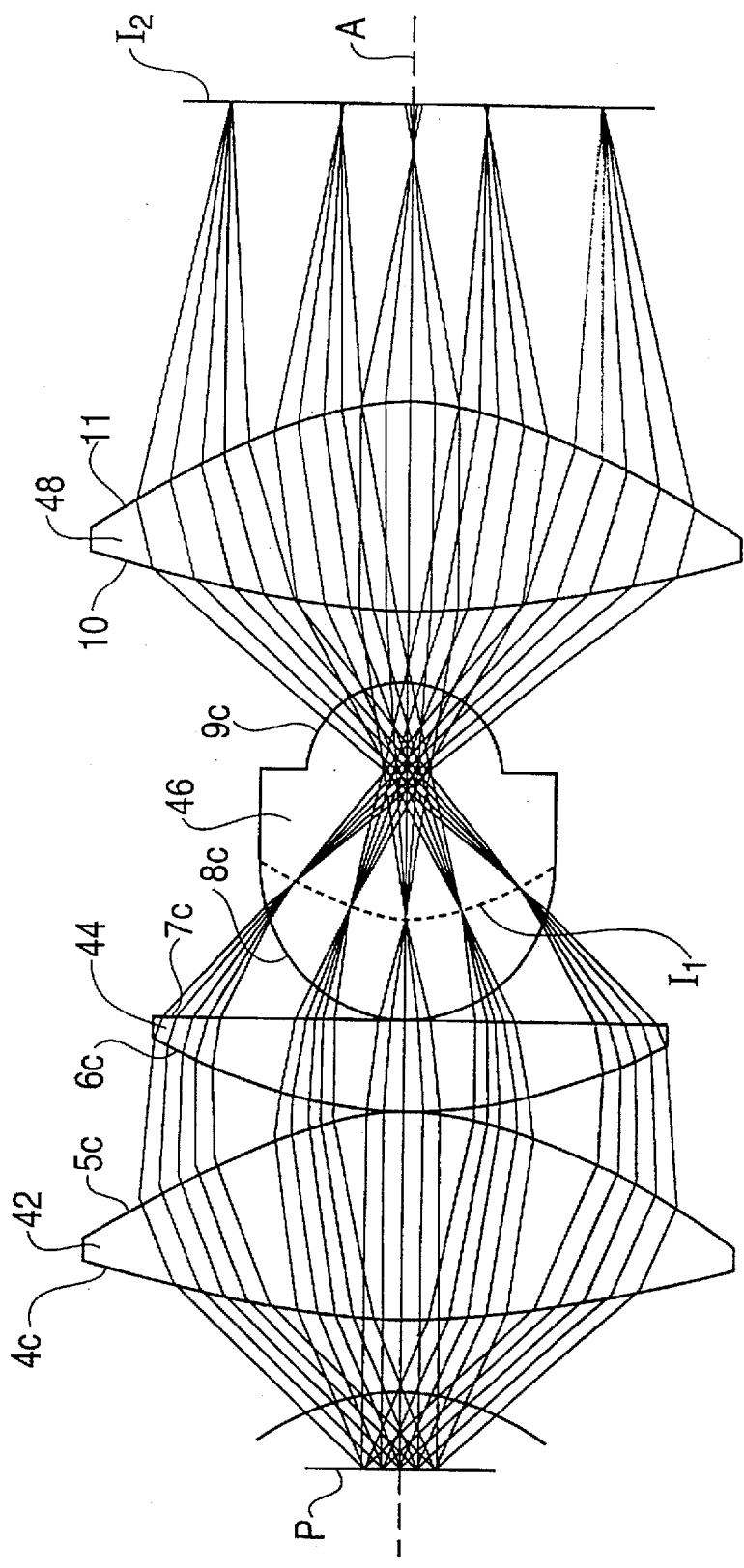
FIG. 6 illustrates a lens layout and ray tracing according to a fourth embodiment of the invention.

FIG. 6 illustrates a further embodiment of the invention which is similar to the embodiment of FIGS. 4 and 5 with the exception that the contact lens element 40 in FIGS. 4 and 5 has been eliminated. FIG. 6 shows a representative corneal surface CS of a patient's eye (not shown) and the corneal apex C. The exemplary characteristics of the lenses and the lens surfaces as described in connection with FIGS. 4 and 5 and shown in Table III also apply to this embodiment, with the exception of the characteristics applying to the contact lens element which is eliminated from this embodiment. Thus, the embodiment of FIG. 6 is not placed in contact with a patient's eye, but rather is either handheld or mounted between the corneal surface CS of a patient's eye and a biomicroscope through which the real, erect image in plane $I_2$ is viewed.

Figure 7:
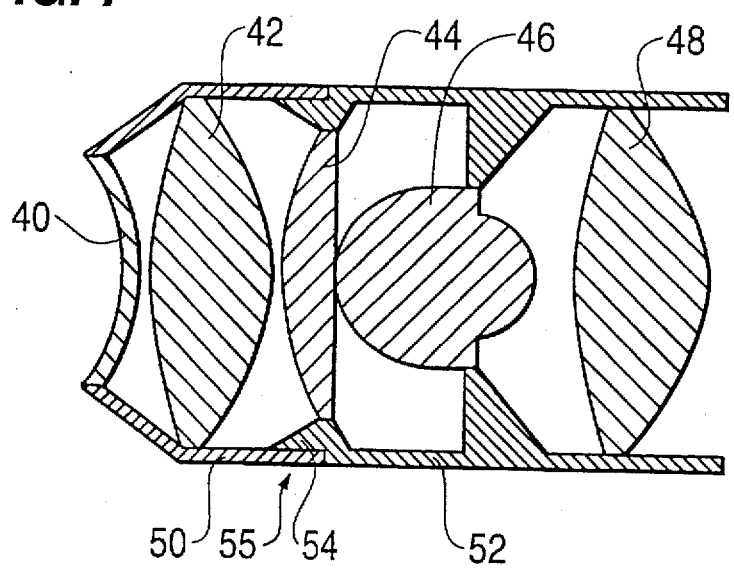
FIG. 7 is a longitudinal sectional view of an embodiment similar to that of FIGS. 4 and 5 and additionally showing a holder securing and interconnecting the lenses.

FIG. 7 is a longitudinal section of an indirect ophthalmoscopy contact lens device which has a lens layout according to the embodiment of FIGS. 4 and 5, with the lenses being mounted in a frame or holder which may comprise a unitary holder or, as shown in FIG. 7, a two-part holder. As shown in this figure, contact lens element 40 and biconvex lens 42 are fixed in a first holder part 50 which is generally conically shaped and includes means for securing and interconnecting lenses 40 and 42 in a conventional manner. Lenses 44, 46 and 48 are secured and interconnected relative to one another by a conventional releaseable attachment mechanism 55 in a second holder part 52 which has an attachment end 54 for releaseably attaching second holder part 52 with first holder part 50. The specific attachment mechanism for releaseably attaching parts 50 and 52 may comprise a bayonet attachment, screw mount, or any other conventional releaseable attachment, the details of which need not be illustrated. According to this aspect of the invention, first holder part 50 with lens 40 and 42 may be used alone in a customary manner for producing an inverted and reversed image of a patient's fundus, or in combination with second holder part 52 with lens 44, 46 and 48 attached as shown in FIG. 7 for producing a real, erect image of the fundus as previously described, viewable with a slit lamp or other biomicroscope.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. An indirect ophthalmoscopy lens device, comprising:
   a first lens system adapted for placement adjacent a patient's eye for capturing light rays emanating from the fundus of the patient's eye and exiting through the cornea of the patient's eye for creating a first, real, inverted image of the patient's fundus outside of the eye; and
   a second lens system located anterior of the first lens system and including a lens which is positioned so that the first real, inverted image produced by the first lens system is contained, at least in part, within said lens, the second lens system bending the rays toward a conjugate pupil region where the rays cross the optical axis of the device and are focused by the second lens system to form a real, reinverted image of the patient's fundus anterior of the second lens system.

2. The device according to claim 1, wherein the first lens system includes a contact lens element having a concave posterior surface which has a curvature adapted for placement on a cornea of a patient's eye.

3. The device according to claim 2, wherein the contact lens element comprises a compound contact lens element having a posterior portion and an anterior portion, said posterior and anterior portions having complementary mating surfaces that are fixed together by an optical glue.

4. The device according to claim 1, wherein the intermediary, real, inverted image is wholly contained within said lens.

5. The device according to claim 1, wherein the conjugate pupil location where the light rays cross the optical axis of the device is contained, at least partially, within a lens of the second lens system.

6. The device according to claim 1, and further including a lens holder for securing and interconnecting the first and second lens systems.

7. The device according to claim 6, wherein the lens holder comprises a first lens holder part for securing the first lens system and a second lens holder part for securing the second lens system, and connecting means for releaseably connecting the first and second lens holder parts together.

8. An indirect ophthalmoscopy lens device, comprising:
   a first lens system adapted for placement adjacent a patient's cornea for capturing light rays emanating from the fundus of the patient's eye and exiting through the cornea of the patient's eye for creating a first real inverted image of the patient's fundus outside the eye; and
   a second lens system located anterior of the first lens system for bending light rays proceeding from the first lens system toward a conjugate pupil location where the rays cross the optical axis of the system and are focused by the second lens system to form a real, reinverted image of the patient's fundus anterior of the second lens system, wherein the conjugate pupil location is contained, at least partially, within a lens of the second lens system.

9. The device according to claim 8, and further including a lens holder for securing and interconnecting the first and second lens systems.

10. The device according to claim 9, wherein the lens holder comprises a first lens holder part for securing the first lens system and a second lens holder part for securing the second lens system, and connecting means for releasably connecting the first and second lens holder parts together.

11. An indirect ophthalmoscopy lens device including a plurality of lenses for collecting light emanating from a patient's eye and focussing the light to form a first, real, inverted image of the fundus of the patient's eye outside of the eye, and for reinverting the first, real, inverted image to form an erect image anterior of the device, wherein the first, real, inverted image is formed at least partially within one of the plurality of lenses of the device.

12. The device according to claim 11, wherein the plurality of lenses includes a contact lens element having a concave posterior surface which has a curvature adapted for placement on a cornea of a patient's eye.

13. The device according to claim 12, wherein the contact lens element comprises a compound contact lens element having a posterior portion and an anterior portion, said posterior and anterior portions having complementary mating surfaces that are fixed together by an optical glue.

14. The device according to claim 11, wherein the first, real, inverted image is wholly contained within the one lens.

15. The device according to claim 11, wherein a conjugate pupil area where the light rays cross an optical axis of the device is contained, at least partially, within a lens of the device.

16. An indirect ophthalmoscopy lens device including a plurality of lenses for collecting light emanating from a patient's eye and focussing the light to form a first real, inverted image of the fundus of the patient's eye outside of the eye and for reinverting the first, real, inverted image to form an erect image anterior of the device, wherein the conjugate image of the patient's pupil is formed within one of the plurality of lenses of the device.

17. The device according to claim 16, wherein the plurality of lenses includes a contact lens which has a curvature adapted for placement on the cornea of a patient's eye.

* * * * *